United States Patent [19]

Keller

[11] Patent Number: 5,003,078

[45] Date of Patent: Mar. 26, 1991

[54] SYNTHESIS OF PHTHALONITRILE RESINS CONTAINING ETHER AND IMIDE LINKAGES

[75] Inventor: Teddy M. Keller, Alexandria, Va.

[73] Assignee: The United States of America as represented by the Secretary of the Navy, Washington, D.C.

[21] Appl. No.: 352,327

[22] Filed: May 16, 1989

[51] Int. Cl.$^5$ .............................................. C07D 487/04
[52] U.S. Cl. .................................. 548/406; 548/418; 548/423; 548/461; 548/433
[58] Field of Search ................ 548/418, 423, 433, 461, 548/406

[56] References Cited

U.S. PATENT DOCUMENTS

| | | | |
|---|---|---|---|
| 3,093,656 | 6/1963 | Dreher et al. | 548/433 |
| 3,927,027 | 12/1975 | Jones et al. | 548/461 X |
| 3,996,196 | 12/1976 | D'Alellio | 428/435 X |
| 4,223,123 | 9/1980 | Keller et al. | 528/210 |
| 4,226,801 | 10/1980 | Keller et al. | 260/465 F |
| 4,234,712 | 11/1980 | Keller et al. | 528/9 |
| 4,238,601 | 12/1980 | Keller et al. | 528/206 |
| 4,244,857 | 1/1981 | Serafini et al. | 548/461 X |
| 4,259,471 | 3/1981 | Keller et al. | 528/9 |
| 4,408,035 | 10/1983 | Keller | 528/103 |
| 4,409,382 | 10/1983 | Keller | 528/173 |
| 4,435,323 | 3/1984 | D'Alelio et al. | 548/423 X |
| 4,499,260 | 2/1985 | Achar et al. | 528/229 |
| 4,587,325 | 5/1986 | Keller | 528/172 |

FOREIGN PATENT DOCUMENTS

| | | | |
|---|---|---|---|
| 40-9018 | 5/1965 | Japan | 548/461 |
| 63-150283 | 6/1988 | Japan | 548/433 |
| 322342 | 2/1972 | U.S.S.R. | 548/461 |
| 1214642 | 2/1970 | United Kingdom | 548/423 |
| 2030983 | 4/1980 | United Kingdom | 548/418 |

OTHER PUBLICATIONS

Keller et al., "Polymerization of Polysulphone Phthalonitriles", Polymer Communications, vol. 26, Feb. 1985, pp. 48–50.

Keller et al., "High Temperature Intrinsically Conductive Polymer", Polymer Communications, vol. 28, Dec. 1987, pp. 334–336.

Keller, "High Temperature Imide-Containing Phthalonitrile Resin", Polymeric Materials Science and Engineering, vol. 58, 1988, pp. 1039–1041.

Keller et al., "Amine-Cured Bisphenol-Linked Phthalonitrile Resins", Journal of Macromolecular Science, A18(6), 1982, pp. 931–937.

Primary Examiner—Joseph Paul Brust
Attorney, Agent, or Firm—Thomas E. McDonnell; Barry A. Edelberg

[57] ABSTRACT

Imide-containing phthalonitrile monomers are prepared from a phthalonitrile and an aromatic dianhydride. The monomer and a method for preparing the monomer is disclosed. These monomers are synthesized into heat resistant polymers and copolymers with aromatic ring structure incorporating imide and ether linkages. The synthesis of the high temperature thermosetting polymers and copolymers is also disclosed.

11 Claims, No Drawings

SYNTHESIS OF PHTHALONITRILE RESINS CONTAINING ETHER AND IMIDE LINKAGES

BACKGROUND OF THE INVENTION

1. Field of the Invention

This invention relates, in general, to high temperature materials and, in particular, to a new class of aromatic phthalonitrile monomers containing ether and imide linkages and their conversion to high temperature thermosetting polymers and copolymers and the synthesis thereof.

2. Description of the Prior Art

Interest in fiber-reinforced composites for advanced aerospace applications has led to the search for high temperature polymers that are easily processed and exhibit high thermal and oxidative stability. Presently, epoxies and polyimides are used. These materials have superior mechanical properties and are lighter and more economical to produce than metals but lack the thermal stability to operate at high temperatures and tend to oxidize and become brittle over time. Conventional epoxy-based composites and adhesives are limited to 120° C. maximum, have a problem with water absorption and require low temperature prepreg storage. Polyimides can produce gaseous products when cured, resulting in voids and blisters in composite components.

Phthalonitrile polymers constitute a recent and important class of high-temperature materials, having a wide range of uses, such as composite matrices, adhesives, sealants, and even semiconductors. These polymers are prepared from phthalonitriles in which the linking group between the two ortho dinitrile groups separates the dinitrile groups enough to permit polymerization. Presently several bridging groups are known. Examples include aliphatic and unsaturated groups, aromatic groups, aliphatic and aromatic diamide groups, and aliphatic and aromatic ether, sulfone and ketone groups.

The chemical and physical properties of the polymers depend primarily on the bridging groups. The groups providing the best properties are those with aromatic, polar and flexible moieties, especially the —O—φ—φ—O— group of U.S. Pat. No. 4,259,471 by Keller et al, the —O—φ—$C_3F_6$—φ—O— of U.S. Pat. No. 4,238,601 by Keller et al, the —O—φ—$C_3$—$H_6$—φ—O— group of U.S. Pat. No. 4,223,123 by Keller el at, the —O—φ—$SO_2$—φ—O— and —O—φ—(C=O)—φ—O— groups of U.S. Pat. No. 4,234,712 by Keller el at and the —O—$C_n$—$H_{2n}$—O— group of U.S. Pat. No. 4,226,801 by Keller el al. These polymers have exceptional thermal and oxidative stability, low water absorptivity, high strength, good dimensional integrity and strong adhesion. The aromatic moieties provide the high mechanical strength, modulus and high thermal and oxidative stability and the polar moieties provide the excellent adhesive properties.

U.S. Pat. No. 4,408,035 teaches curing of phthalonitrile monomers with a nucleophilic aromatic amine. The monomer, 4,4'-bis(3,4-dicyanophenoxy)biphenyl, has a melting point of 232°–234° C. The aromatic diamines covered in the above patent are somewhat volatile at the required processing melt temperature, causing void problems when used in an amount greater than 5% by weight. It is advantageous for a resin not to produce gaseous products when cured. Also, the chemical makeup of the polymer must be such that it consists of units having known resistance to bond-rupture under thermal, oxidative and hydrolytic conditions.

U.S. patent application Ser. No. 07/273,443 discloses 1,3-bis(3-aminophenoxy)benzene and other bis(aminophenoxy) compounds used as a curing agent for a rapid synthesis of phthalonitrile resin. The time and temperature needed for polymerization of bisphenol-linked phthalonitrile monomers are easily controlled as a function of the concentration of amine curing agent.

The necessity for aromatic and heterocyclic ring structure in a polymer to achieve heat resistance has long been recognized. The ideal heat resistant polymer would be composed of aromatic and/or heteroaromatic ring structures interconnected by flexible linkages within the polymeric backbone to improve processability and to enhance the mechanical properties. However, few synthetic methods are available for incorporating stable linkages into a polymeric system.

SUMMARY OF THE INVENTION

Accordingly, an object of this invention is to synthesize phthalonitrile monomers, polymers and copolymers with excellent thermal and oxidative properties and good mechanical properties in excess of 300° C.

And, an object of this invention is to produce polymeric materials for composite matrices to be used in applications where the use temperature is above the operating temperature for conventional high temperature polymers and below the operating temperature for ceramics or metals.

Also, an object of this invention is to produce polymeric material which are free of voids.

Further, an object of this invention is to provide new type of phthalonitrile resins having aromatic imide and ether linkages in the bridge connecting the terminal phthalonitrile polymerizable units.

Additionally, an object of this invention is to provide a resin which is more resistant to oxidative attack than epoxies, bismaleimides and other conventional thermosetting polyimides.

These and other objects are accomplished by reacting an aminophenoxyphthalonitrile with an aromatic dianhydride to produce an amic acid linked phthalonitrile which can be imidized either by chemical and/or thermal means. The resulting phthalonitrile resin is processed either alone or in the presence of a bisphenol-based phthalonitrile which behaves as a reactive plasticizer. Polymerization of the neat resin or polymeric blend is achieved by heating above the melting point or softening temperature in the absence or presence of aromatic di- or poly-amines, metal and/or metallic salts.

DESCRIPTION OF THE PREFERRED EMBODIMENT

The imide-containing phthalonitrile monomers of this invention are represented by the formula:

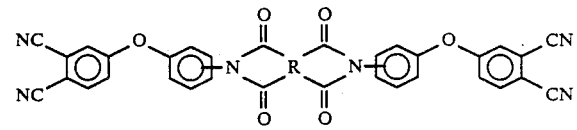

where R is an aromatic tetravalent radical or substituted aromatic tetravalent radical. By the word "substituted", it is meant in this application that any known substituent could be attached to the aromatic moiety. Substituents include but are not limited to halogens, chalcogens and organic radicals, such as phenyl, alcohol, carboxyl, carbonyl, or aliphatic groups of less than 10 carbon atoms. The preferred compounds are where R is an aromatic tetravalent radical of the general formula:

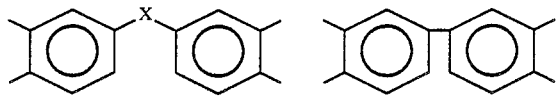

The imide-containing phthalonitrile monomers of this invention are prepared in solution by reaction of their precursors, 4-(3- or 4-aminophenoxy) phthalonitrile and an aromatic dianhydride. The phthalonitrile monomers are synthesized by reaction of 4-(3- or 4aminophenoxy) phthalonitrile with an aromatic dianhydride. Upon isolation by pouring the reaction mixture into an appropriate precipitating solvent such as ethanol, complete imidization is achieved thermally in air at 300° C.

The imide-containing phthalonitrile monomers are prepared from 4-(3- or 4-aminophenoxy)phthalonitrile and an aromatic dianhydride according to the following process:

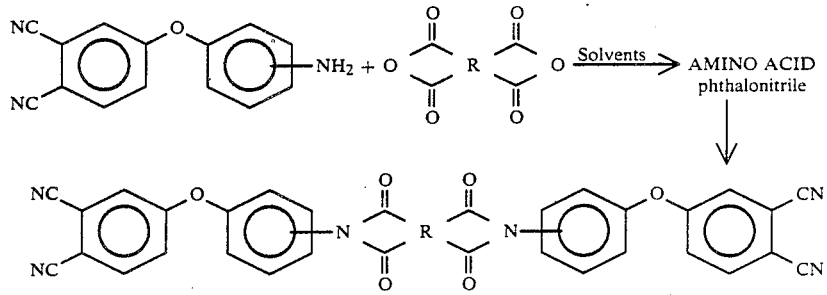

where R is as described above.

The 4-(3- or 4-aminophenoxy)phthalonirile is prepared according to the following process:

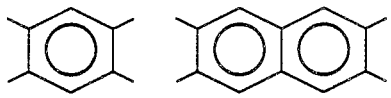
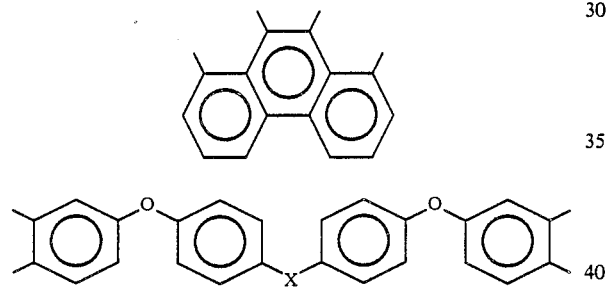

where X is

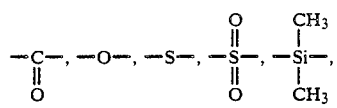

any alkyl of six carbons or fewer or any partially or perhalogenated alkylene of six carbons or fewer.

The most preferred compounds are where R is an aromatic tetravalent radical of the general formula:

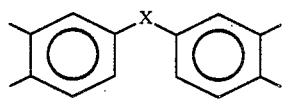

where X is

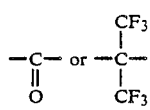

Examples of the preferred dianhydrides which are suitable for use in this invention are listed below:
4,4'-(hexafluoroisopropylidene)diphthalic anhydride
pyrometallitic dianhydride
3,3',4,4'-benzophenonetetracarboxylic dianhydride
2,3,6,7-naphthalene tetracarboxylic dianhydride
3,3',4,4'-diphenyl tetracarboxylic dianhydride
1,3,5,6-naphthalene tetracarboxylic dianhydride
2,2',3,3'-diphenyl tetracarboxylic dianhydride
2,2-bis(3,4-dicarboxyphenyl)propane dianhydride
bis(3,4-dicarboxyphenyl)ether dianhydride
naphthalene-1,2,4,5-tetracarboxylic dianhydride
naphthalene-1,4,5,8-tetracarboxylic dianhydride
decahydronaphthalene-1,4,5,8-tetracarboxylic dianhydride
4,8-dimethyl-1,2,3,5,6,7-hexahydronaphthalene-1,2,5,6-tetracarboxylic dianhydride
2,6-dichloronaphthalene-1,4,5,8-tetracarboxylic dianhydride
2,7-dichloronaphthalene-1,4,5,8-tetracarboxylic dianhydride
2,3,6,7-tetrachloronaphthalene-1,4,5,8-tetracarboxylic dianhydride
phenanthrene-1,8,9,10-tetracarboxylic dianhydride
2,2-bis(2,3-dicarboxyphenyl)propane dianhydride
1,1-bis(2,3-dicarboxyphenyl)ethane dianhydride
1,1-bis(3,4-dicarboxyphenyl)ethane dianhydride
bis(2,3-dicarboxyphenyl)methane dianhydride bis(3,4-dicarboxyphenyl)methane dianhydride
bis(3,4-dicarboxyphenyl)sulfone dianhydride
benzene-1,2,3,4-tetracarboxylic dianhydride
4,4'-oxydiphthalic dianhydride
4,4'-thiophthalic dianhydride The most preferred dianhydrides are 3,3',4,4'-benzophenonetetracarboxylic dianhydride and 4,4'-(hexafluoroisopropylidene)diphthalic anhydride.

The imide-containing phthalonitrile polymers of this invention contain the repeating unit represented by the formula:

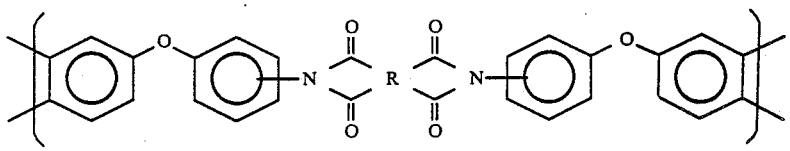

where R is an aromatic tetravalent radical or substituted aromatic tetravalent radical as defined above. The preferred compounds are where R is an aromatic tetravalent radical of the general formula:

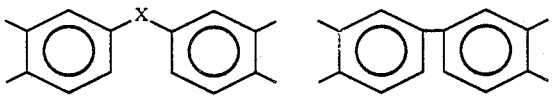

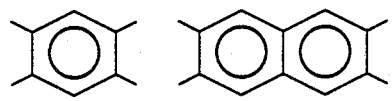

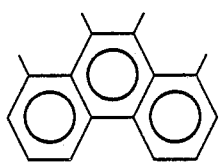

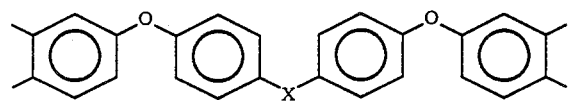

where X is

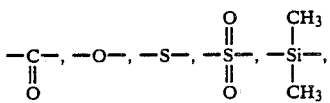

any alkyl of six carbons or fewer or any partially or perhalogenated alkyl of six carbons or fewer.

The most preferred compounds are where R is an aromatic tetravalent radical of the general formula:

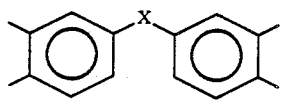

where X is

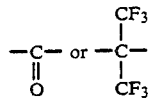

Polymerization of the phthalonitrile monomer is accomplished by heating the monomer mixture above its melting point, continued heating at a temperature above the glass transition temperature of the prepolymer amorphous reactants until the mixture reaches its gelation point, curing the mixture to complete crosslinking of the polymer and postcuring at a temperature from above the glass transition temperature of the polymer up to just below the carbonization temperature. Examples of cure cycles for neat polymerization are (1)a two-part cure of 225°–280° C. for 6–20 hours and 300°–315° C. for 10–20 hours; (2)a three-part cure of 225°–280° C. for 6–16 hours, 240°–300° C. for 2–6 hours and 300°–315° C. for 5–16 hours. The preferred two-part cure is 240° C. for 17 hours and 315° C. for 16 hours. The preferred three-part cure is 225° C. for 16 hours, 280° C. for 6 hours and 315° C. for 16 hours. The most preferred cure is the three-part cure.

The time and temperature needed for polymerization can be reduced by curing phthalonitrile resins in the presence of amine curing agents that are stable at the initially required processing temperatures. These amine curing agents do not volatilize during the polymerization reaction. The amine curing agents are of the general formula $YNH_2$ where Y is an aromatic. The amount of curing agent added should be in the range of 1 to 10 weight percent of the polymer mixture. The preferred amount of curing agent is 1 to 5 weight percent. The most preferred amount of curing agent is 1.5 to 2.0 weight percent.

Specific examples of amine curing agents useful in this invention are given below:
o-phenylenediamine
m-phenylenediamine
p-phenylenediamine
4,4'-diaminodiphenylpropane
4,4'-diaminodiphenylmethane (commonly named 4,4'-methylenedianiline)
4,4'-diaminodiphenyl sulfide (commonly named 4,4'-thiodianiline)
4,4'-diaminodiphenyl ether (commonly named 4,4'-oxydianiline)
1,5-diaminonaphthalene
3,3'-dimethylbenzidine
3,3'-dimethoxybenzidine
2,4-bis(β-amino-t-butyl)toluene
bis(p-β-amino-t-butyl)ether
bis(p-β-methyl-o-aminopentyl)benzene
1,3-diamino-4-isopropylbenzene
1,2-bis(3-aminopropoxy)ethane
benzidine
m-xylylenediamine
p-xylylenediamine
2,4-diaminotoluene
2,6-diaminotoluene
1,3-bis(3-aminophenoxy)benzene
1,3-bis(4-aminophenoxy)benzene
1,4-bis(3-aminophenoxy)benzene
1,4-bis(4-aminophenoxy)benzene
bis[4-(3-aminophenoxy)phenyl]sulfone
bis[4-(4-aminophenoxy)phenyl]sulfone 4,4'-bis(3-aminophenoxy)biphenyl
4,4'-bis(4-aminophenoxy)biphenyl
2,2-bis[4-(3-aminophenoxy)phenyl]propane
2,2-bis[4-(4-aminophenoxy)phenyl]propane The most preferred amine curing agent is 1,3-bis(3-aminophenoxy) benzene (APB).

Examples of cure cycles for polymerization with amine curing agents are (1) a two-part cure of 225°-260° C. for 5-20 hours and 300°-315° C. for 5-20 hours; (2) a three-part cure of 180°-240° C. for 2-16 hours, 240°-300° C. for 2-8 hours and 300°-315° C. for 10-20 hours; (3) a four-part cure of 180°-200° C. for 1-3 hours, 200°-240° C. for 2-4 hours, 240°-280° C. for 4-6 hours and 300°-315° C. for 10-20 hours. The preferred two-part cure is 225° C. for 6 hours and 315° C. for 16 hours. The preferred three-part cure is 225° C. for 16 hours, 280° C. for 6 hours and 315° C. for 16 hours. The preferred four-part cure is 200° C. for 2 hours, 240° C. for 3 hours, 280° C. for 5 hours and 315° C. for 16 hours. The most preferred cure is the three-part cure.

After the cure cycle is complete, a postcure can be carried out to improve the mechanical and thermal properties of the material. The preferred postcure is 325°-365° C. for 2-6 hours and 365°-385° C. for 5-24 hours. The most preferred postcure is 350° C. for 4 hours and 375° C. for 12 hours. When postcure temperatures are in excess of 316° C., heating is under an inert atmosphere, such as nitrogen or argon.

It should be noted that the cure cycles and postcures given above are not intended to be complete and all inclusive. Other cure cycles and postcures are possible depending on variations in time, temperature and additives.

Polymerization and thus processibility phthalonitrile monomers are somewhat difficult due to the enhanced viscosity of these monomers compared to the bisphenol-based phthalonitrile of U.S. patent application Ser. No. 07/273,443. A reduction in the viscosity was achieved by copolymerizing the imide-containing phthalonitrile with these bisphenol-based phthalonitriles. The bisphenol-based phthalonitriles behave as reactive plasticizer. As the term implies, the role of the reactive plasticizer is to improve the processability and then, through reaction with the imide-containing phthalonitriles and itself, become a part of the cured resin system. Blends of imide-containing phthalonitrile and bisphenol-based phthalonitrile can be fabricated without seriously compromising the use properties. The amount of bisphenol-based phthalonitrile is in the range from 10% to 50% by weight. The preferred amount is in the range from 20% to 30% by weight. The most preferred amount is approximately 25% by weight.

A general formula of the bisphenol-based phthalonitrile useful as a reactive plasticizer is shown below:

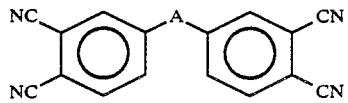

where A is any divalent organic radical, for example, a bisphenol group, a diether group or a dithioether group. The preferred diphthalonitrile monomers are those in which A in the formula above is a diether group, —O—R'—O. The most preferred diphthalonitrile monomers are those wherein R' is selected from the class consisting of

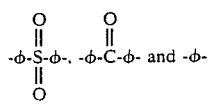

$$-\phi-C_3H_6-\phi-, \quad -\phi-C_3F_6-\phi-, \quad -C_aH_{2a}-, \quad -\phi-\phi-,$$

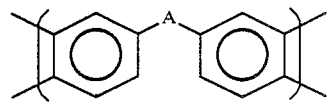

wherein $\phi$ is a phenyl group, wherein the phenyl groups are linked at the para and the meta positions and wherein "a" is any integer. The bisphenol-containing phthalonitrile monomers copolymerize with the imide-containing phthalonitrile monomers to form a copolymer with the following repeating unit:

It is possible with the present invention to include a metal or metal salt in the resins. For composite fabrication, a salt or a metal would be less desirable because of problems with homogeneity and gassing. Examples of suitable metal salts include cuprous chloride, cuprous bromide, cuprous cyanide, cuprous ferricyanide, zinc chloride, zinc bromide, zinc iodide, zinc cyanide, zinc ferrocyanide, zinc acetate, zinc sulfide, silver chloride, ferrous chloride, ferric chloride, ferrous ferricyanide, ferrous chloroplatinate, ferrous fluoride, ferrous sulfate, cobaltous chloride, cobaltic sulfate, cobaltous cyanide, nickel chloride, nickel cyanide, nickel sulfate, nickel carbonate, stannic chloride, stannous chloride hydrate, a complex of triphenylphosphine oxide and stannous chloride (2TPPO/SnCl$_2$) and mixtures thereof. The metals which can used include chromium, molybdenum, vanadium, beryllium, silver, mercury, aluminum, tin, lead, antimony, calcium, barium, manganese, magnesium, zinc, copper, iron, cobalt, nickel, palladium and platinum. Mixtures of these metal may also be used. The preferred metals are copper, silver and iron.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE I

Synthesis of Imide-Containing Phthalonitrile from 3,3',4,4'-benzophenonetetracarboxylic dianhydride (BTDA) and 4-(3-aminophenoxy)phthalonitrile To a 100 ml three-necked flask was added 3,3',4,4'-benzophenonetetracarboxylic dianhydride (5.4 g, 16.7 mmol) and 30 ml of dry dimethylformamide (DMF). After flushing the solution with nitrogen for 20 minutes, 4-(3-aminophenoxy) phthalonitrile (7.8 g, 33.3 mmol) was added under ambient conditions. The temperature of the reaction mixture was increased to 90° C. and held at this temperature for 1 hour. Toluene (30 ml) was added and the solution was heated to reflux. The water which was formed as a by-product was azeotroped from the mixture with a Dean Stark trap. Total reflux time was 12 hours. After removing the toluene by distillation and cooling, the white solidified product mixture was removed from the reaction vessel washed with ethanol, collected by filtration, dried and annealed at 200° C. for 2 hours to afford 11.9 g (93%) of imide-containing phthalonitrile, m.p. 245°–248° C.

EXAMPLE II

Synthesis of 6F Imide-Containing Phthalonitrile from 4,4'-(hexafluoroisopropylidene)diphthalic Anhydride and 4-(3-aminophenoxy)phthalonitrile To a 100 ml three necked flask was added 4,4'-hexafluoroisopropylidene)diphthalic anhydride (5.0 g, 11.3 mmol) and 30 ml of dry dimethylformamide (DMF). After thoroughly flushing the solution with nitrogen, 4-(3-aminophenoxy) phthalonitrile (5.3 g, 22.3 mmol) was added under ambient conditions. The temperature of the reaction mixture was increased to 90° C. and held at this temperature for 1 hour. Toluene (30 ml) was added and the solution was heated to reflux. Water as formed was azeotroped from the mixture with a Dean-Stark trap. After refluxing for 12 hours, the toluene was removed by distillation. Upon cooling the product mixture was removed from the reaction vessel, washed several times with ethanol, collected by suction filtration, dried and annealed at 200° C. for 4 hours to complete the imidization reaction resulting in the formation of an amorphous material.

EXAMPLE III

Neat Polymerization of BTDA-Derived Imide Phthalonitrile

A 1 g sample of the imide-containing phthalonitrile was placed in an aluminum planchet and degassed in a specially designed desiccator for evacuation purposes at 280° C. for 3 hours. The viscous monomer was then placed in a oven preheated to 280° C. and cured in air by heating at 280° C. for 17 hours (overnight) and at 315° C. for 16 hours. Upon cooling the polymer was removed from the planchet and found to be void-free. A portion of the polymer was then postcured under an oxygen-free argon atmosphere at 350° C. for 4 hours and at 375° C. for 12 hours. The thermal and oxidative properties were enhanced as a result of the postcure treatment.

EXAMPLE IV

Polymerization of BTDA-Derived Imide Phthalonitrile with Amine Additive

A 1.0 g sample of BTDA-imide-containing phthalonitrile was placed in an aluminum planchet and degassed at 300.C for 4 hours in a specially designed desiccator for evacuation purposes. After cooling to 250° C., 1,3-bis(3-aminophenoxy)benzene (APB, 2% by weight) was added to the viscous sample with stirring. After 2 hours at 250° C., the sample had gelled and become rubbery. The sample was then heated at 280° C. for 6 hours and at 315° C. for 16 hours (overnight). Thermogravimetric analysis (TGA) of powdered samples under both air and inert atmospheres showed no decomposition before 350° C. Between 550°–650° C., catastrophic oxidative degradation occurred. At 800° C. under a nitrogen atmosphere, the polymer exhibited a char yield of 60%.

EXAMPLE V

Polymerization of BTDA-Derived Imide Phthalonitrile with Amine Additive

A 0.5 g sample of BTDA-imide-containing phthalonitrile was placed in an aluminum planchet and degassed at 300° C. for 3 hours as in Example III. At this time, the sample was cooled to 210° C. and APB (5 mmol, 1% by weight) was added with stirring to the viscous monomer. The sample was then placed in an oven and cured by heating at 200° C. for 2 hours, at 220° C. for 3 hours and at 260° C. for 5 hours and at 315° C. for 16 hours. The sample exhibited a glass transition temperature ($T_g$) of 177° C. as determined by differential scanning calorimeter (DSC). When further postcured in a sequence under an oxygen-free argon atmosphere at 350° C. for 4 hours and at 375° C. for 12 hours, the sample did not exhibit a $T_g$.

EXAMPLE VI

Polymerization of BTDA-Derived Imide Phthalonitrile with Stannous Chloride

A 0.5 g sample of the BTDA-imide-containing phthalonitrile was placed in an aluminum planchet and degassed as in Example III. To the melt as 260° C. was added $SnCl_2.H_2O$ (0.035 g, 7% by weight) with stirring. The viscosity started to increase rapidly. Full gelation had occurred within 3 minutes. To complete the cure, the sample was heated at 260° C. for 6 hours and a 300° C. for 16 hours. Upon cooling, the polymer was removed from the planchet and appeared tough.

To another sample of the monomer (0.5 g) was added $SnCl_2.H_2O$ (0.018 g, 3.6% by weight) with stirring at 260° C. Solidification occurred within 5 minutes at 260° C. To complete the cure the sample was heated at 260° C. for 6 hours and at 315° C. for 16 hours.

To a third sample of the monomer (0.5 g) was added $SnCl_2.H_2O$ (0.005 g, 1% by weight) with stirring at 260° C. Full gelation was somewhat slower. Solidification had occurred after 20 minutes. To complete the cure, the sample was heated at 260° C. for 2 hours and at 315° C. for 16 hours.

EXAMPLE VII

Polymerization of 6F Imide-Containing Phthalonitrile with Amine Additive

A 0.5 g sample of the 6F imide-containing phthalonitrile was placed in a aluminum planchet and degassed as in Example III. To the melt was added 0.01 g of APB (2% by weight) with stirring. The sample was cured by heating at 260° C. for 3 hours and at 300° C. for 5 hours and at 315° C. for 10 hours. The polymer showed excellent thermo-oxidative stability as determined by TGA with the initial weight loss commencing at about 450° C. and the catastrophic decomposition occurring between 500°–700° C. In an inert atmosphere, the polymer exhibited a char yield of 60% at 800° C. When the polymer was postcured in sequence under an oxygen-free argon atmosphere at 350° C. for 4 hours and at 375° C. for 12 hour, it was found not to exhibit a $T_g$. Moreover, an enhancement in the thermooxidative stability was observed with initial weigh loss commencing at temperature in excess of 500° C. No improvements in the thermal stability was observed.

EXAMPLE VIII

Copolymer of BTDA-Derived Imide Phthalonitrile and 4,4'-Bis(3,4-dicyanophenoxy)biphenyl Cured Neat A sample containing 0.8 g of BTDA-imide-containing phthalonitrile and 0.2 g of 4,4'-bis(3,4-dicyanophenoxy)biphenyl was thoroughly mixed in an aluminum planchet and degassed in the melt at 260°–280° C. for 4 hours at reduced pressure in a specially designed desiccator for evacuation purposes. The monomeric blend, whose viscosity was considerably reduced relative to the neat BTDA-imide-containing phthalonitrile itself, was cured by heating in air at 225° C. for 16 hours, at 280° C. for 6 hours and at 315° C. for 16 hours. The blend solidified during the 225° C. heat treatment. The copolymer showed similar thermal and oxidative properties as found for the polymer derived solely from the BTDA-imide-containing phthalonitrile polymer. When the copolymer was further post cured in sequence at 350° C. for 4 hours and at 375° C. for 12 hours, it was found not to exhibit a $T_g$.

EXAMPLE IX

Copolymer of BTDA-Derived Imide Phthalonitrile and 4,4'-Bis(3,4-dicyanophenoxy)biphenyl Cured with Amine Additive A sample containing 0.8 g of BTDA-imide-containing phthalonitrile and 0.2 g of 4,4'-bis(3,4-dicyanophenoxy)biphenyl was mixed in a aluminum planchet and degassed as in Example VIII. To the melt of the blend was added 0.01 g of APB at 240° C. with stirring. The monomeric blend was then cured by heating in air at 225° C. for 16 hours (overnight), at 280° C. for 8 hours and at 315° C. for 16 hours. Gelation occurred during the 225° C. heat treatment.

EXAMPLE X

Copolymer of BTDA-Derived Imide Phthalonitrile (70%) and 4,4'-bis(3,4-dicyanophenoxy)biphenyl (30%) Cured with 2% By Weight of Amine Additive A sample containing 0.70 g of BTDA-imide-containing phthalonitrile and 0.30 g of 4,4'-bis(3,4-dicyanophenoxy)biphenyl was mixed in a aluminum planchet and degassed as in Example VIII. The fluidity of the mixture was such that it was easy to process the sample above 200° C. To the melt at 225° C. was added 0.02 g (2% by weight) of APB with stirring. The monomeric blend was then cured in air by heating at 225° C. for 6 hours, at 280° C. for 2 hours and at 315° C. for 16 hours. Gelation occurred during the 225° C. heat treatment.

EXAMPLE XI

Copolymer of BTDA-Derived Imide Phthalonitrile (70%) and Bis[4-(3,4-dicyanophenoxy)phenyl]2,2-propane (30%) Cured with 3% By Weight of Amine Additive A sample containing 0.70 g of BTDA-imide-containing phthalonitrile and 0.30 g of bis[4-(3,4-dicyanophenoxy)phenyl]2,2-propane was mixed in an aluminum planchet and degassed as in Example VIII. Due to the low viscosity of the mixture in the melt relative to that of pure BTDA-imide-containing phthalonitrile monomer, the resulting mixture was easily processed above 200° C. To the melt of the monomeric blend at 225.C was added 0.03 g of APB (3% by weight). The mixture was stirred for 15 minutes. The mixture was then cured in air at 225° C. for 16 hours and at 315 for 6 hours.

EXAMPLE XII

Copolymer of BTDA-Derived imide Phthalonitrile (70%) and Bis[4-(3,4-dicyanophenoxy)phenyl] Sulfone (30%) Cured With 2% By Weight of Amine Additive)

A sample containing 0.70 g of BTDA-imide-containing phthalonitrile and 0.30 g of bis[4-(3,4-dicyanophenoxy)phenyl]sulfone was placed in an aluminum planchet and degassed as in Example VIII. To the melt of the monomeric blend was added 0.02 g of methylenedianiline (MDA) with stirring. The mixture was cured by heating in air at 225° C. for 4 hours, at 280° C. for 4 hours and at 315° C. for 10 hours. Gelation occurred during the heat treatment at 225° C.

EXAMPLE XIII

Copolymer of BTDA-Derived imide Phthalonitrile (50%) and Bis[4-(3,4-dicyanophenoxy)phenyl] Sulfone (50%) Cured with 2% By Weight of Amine Additive)

A sample containing 0.50 g of BTDA-imide-containing phthalonitrile and 0.50 g of bis[4-(3,4-dicyanophenoxy)phenyl)sulfone was placed in an aluminum planchet and degassed as in Example VIII. To the low viscosity melt at 200° C. was added 0.02 g of 1,3-bis(4-aminophenoxy)benzene with stirring. Soon after the addition of the amine compound, the temperature of the mixture was reduced to 160° C. resulting in the reaction blend becoming somewhat viscous. After stirring the monomeric blend at 160° C. for 30 minutes, it was placed in an oven preheated to 200° C. Gelation had occurred after 2 hours at 200° C. To complete the cure, the sample was further heated in air at 260° C. for 8 hours and at 300° C. for 16 hours.

EXAMPLE XIV

Copolymer of 6F Imide-Containing Phthalonitrile (70%) and Bis4-(3,4-dicyanophenoxy)phenyl]b 2,2-hexafluoropropane (30%) Cured Neat A sample containing 0.70 g of 6F imide-containing phthalonitrile and 0.30 g of bis[4-(3,4 dicyanophenoxy)phenyl]2,2-hexafluoropropane was placed in an aluminum planchet and degassed as in Example VIII. The resulting monomeric blend was cured by heating in air at 240° C. for 16 hours (overnight), at 280° C. for 2 hours, and at 315° C. for 6 hours. Gelation occurred during the 240° C. heat treatment.

EXAMPLE XV

Copolymer of 6F Imide-Containing Phthalonitrile (60%) and Bis4-(3,4-dicyanophenoxy)phenyl]2,2-Hexafluoropropane (40%) with 1.5% By Weight of Amine Additive A sample containing 0.50 g of 6F imide-containing phthalonitrile and 0.40 g of bis[4-(3,4-dicyanophenoxy)phenyl]2,2hexafluoropropane was placed in an aluminum planchet and degassed as in Example VIII. To the melt of the monomeric blend at 200° C. was added 0.15 g of APB with stirring. After stirring for 10 minutes at 200° C., the sample was placed in an oven and cured by heating in air at 180° C. for 4 hours, at 240° C. for 4 hours and at 300° C. for 20 hours.

The new phenoxy- and imide-containing polymers exhibit outstanding thermo-oxidative stability and have potential usage for aerospace composite applications in the 300°-375° C. range. Such material could bridge the gap between currently used high temperature polymers and ceramics and metal.

During polymerization of the new phthalonitrile resins containing ether and imide linkages, no volatiles are formed, resulting in void-free components. The new resins exhibit better thermo-oxidative properties than current commercially available high temperature materials, such as PMR-15 and Thermid 600. The mechanical properties of the new resins should be improved due to a reduction in the crosslinking density.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A monomer of the formula:

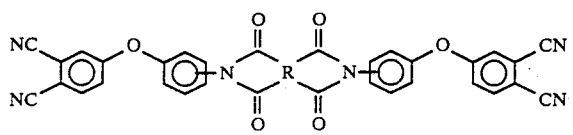

where R is an tetravalent radical or substituted aromatic tetravalent radical of the general formula:

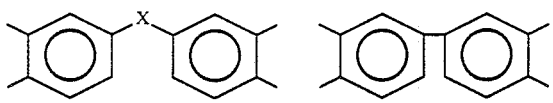

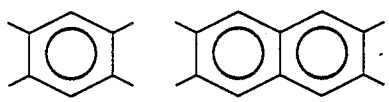

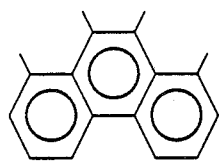

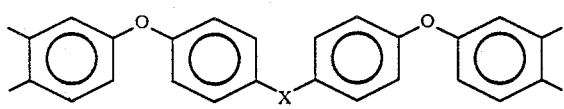

where X is

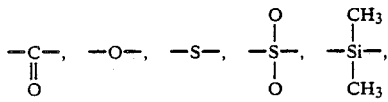

any alkylene of up to six carbon atoms or any halogenated alkylene of up to six carbon atoms.

2. A monomer as recited in claim 1 wherein R is an aromatic tetravalent radical or substituted aromatic tetravalent radical of the general formula:

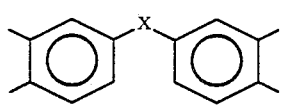

where X is

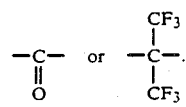

3. A monomer according to claim 1, and produced by reacting an aromatic dianhydride with 4-(3-aminophenoxy)phthalonitrile to produce said monomer.

4. A monomer as recited in claim 3 wherein the aromatic dianhydride is chosen from the group consisting of 4,4'-(hexafluoroisopropylidene)diphthalic anhydride, pyromellitic dianhydride, 3,3',4,4'-benzophenonetetracarboxylic dianhydride, 2,3,6,7-naphthalenetetracarboxylicdianhydride, 3,3',4,4'-diphenyl tetracarboxylic dianhydride, 1,3,5,6-naphthalene tetracarboxylic dianhydride, 2,2'3,3'-diphenyl tetracarboxylic dianhydride, 2,2-bis(3,4-dicarboxyphenyl)propane dianhydride, bis(3,4-dicarboxyphenyl)ether dianhydride, naphthalene-1,2,4,5-tetracarboxylic dianhydride, naphthalene-1,4,5,8-teracarboxylic dianhydride, decahydronaphthalene-1,4,5,8-tetracarboxylic dianhydride, 4,8-dimethyl-1,2,3,5,6,7-hexahydronaphthalene-1,2,5,6-tetracarboxylic dianhydride, 2,6-dichloronaphthalene-1,4,5,8-tetracarboxylic dianhydride, 2,7-dichloronaphthalene-1,4,5,8-tetracarboxylic dianhydride, 2,3,6,7-tetrachloronaphthalene-1,4,5,8-teracarboxylic dianhydride, phenanthrene-1,8,9,10-tetracarboxylic dianhydride, 2,2-bis(2,3-dicarboxyphenyl)propane dianhydride, 1,1-bis(2,3-dicarboxyphenyl)ethane dianhydride, 1,1-bis(3,4-dicarboxyphenyl)ethane dianhydride, bis)2,3-dicarboxyphenyl)methane dianhydride, bis(3,4-dicarboxyphenyl)methane dianhydride, bis(3,4-dicarboxyphenyl)sulfone dianhydride, benzene-1,2,3,4-tetracarboxylic dianhydride, 4,4'-oxydiphthalic dianhydride and 4,4'-thiophthalic dianhydride.

5. A monomer as recited in claim 4 wherein the aromatic dianhydride is 3,3',4,4'-benzophenonetetracarboxylic dianhydride.

6. A monomer as recited in claim 4 wherein the aromatic dianhydride is 4,4'-(hexafluoroisopropylidene)-diphthalicanhydride.

7. A monomer as recited in claim 5 wherein the phthalonitrile is 4-(3-aminophenoxy) phthalonitrile.

8. The monomer of claim 1, wherein, when X is a halogenated alkylene, said halogenated alkylene is perhalogenated.

9. A monomer as recited in claim 1, where X is

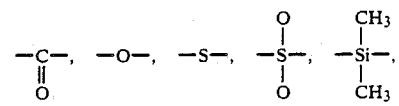

any alkylene of up to six carbon atoms, any fluorinated alkylene of up to six carbon atoms, any chlorinated alkylene of up to six carbon atoms, or any bromated alkylene of up to six carbon atoms.

10. The monomer of claim 9, wherein, when X is a halogenated alkylene, said halogenated alkylene is perhalogenated.

11. The monomer of claim 1, wherein X is

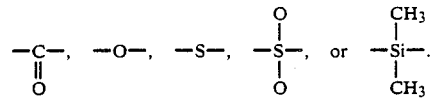

* * * * *